United States Patent
Goodwin, Jr.

(10) Patent No.: US 6,329,164 B1
(45) Date of Patent: *Dec. 11, 2001

(54) METHOD FOR USING A CELL ACTIVITY ASSAY APPARATUS

(75) Inventor: Richard H. Goodwin, Jr., Bethesda, MD (US)

(73) Assignee: Neuro Probe, Incorporated, Gaithersburg, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/271,765

(22) Filed: Mar. 18, 1999

(51) Int. Cl.⁷ ..................................................... C12Q 1/02

(52) U.S. Cl. ................................................ 435/29; 435/30

(58) Field of Search .................... 435/4, 29, 30, 435/287.7, 287.8, 288.2, 297.1, 297.2

(56) References Cited

U.S. PATENT DOCUMENTS

| | | | |
|---|---|---|---|
| 3,888,770 | 6/1975 | Avital et al. | 210/238 |
| 3,929,583 | 12/1975 | Sharpe et al. | 195/127 |
| 4,317,726 | 3/1982 | Shepel | 210/236 |
| 4,493,815 | 1/1985 | Fernwood et al. | 422/101 |
| 4,514,495 | 4/1985 | Schalkowsky et al. | 435/32 |
| 4,714,674 | 12/1987 | Palladino et al. | 435/18 |
| 4,912,057 | 3/1990 | Guirguis et al. | 435/285 |
| 5,137,023 * | 8/1992 | Mendelson et al. | 128/633 |
| 5,210,021 | 5/1993 | Goodwin, Jr. | 435/29 |
| 5,284,753 | 2/1994 | Goodwin, Jr. | 435/30 |
| 5,302,515 | 4/1994 | Goodwin, Jr. | 435/29 |
| 5,601,997 * | 2/1997 | Tchao | 435/29 |
| 5,614,719 * | 3/1997 | Hayes et al. | 250/343 |

OTHER PUBLICATIONS

Frevert C. Rapid Fluorescence Based Measurement of Neutrophil Migration in Vitro, J of Immunological Methods 213(1)41–52, Jan. 1998.*

Stephen Boyden Ph.D., "The Chemotactic Effect of Mixtures of Antibody and Antigen on Polymorphonucleat Leucocytes" J. Exp. Med. 115:pp. 453–466, (1962).

Zicha et al., A New Direct Viewing Chemotaxis Chamber, Journal of a Cell Science 99, 769–775 (1991).

Wilkinson, Microscope Filter Methods for Leukocyte Chemotaxis, Methods in Enzymology 162, 38–50(1998).

NeuroProbe MB Series Microtiter Plate Chambers, Neuroprobe, Inc. (1994).

S.H. Zigmond and D.A. Lauffenburger, Assays of Leukocyte Chemotaxis Annual Review of Medicine. 37, pp. 149–155.

B. Gatewood, J. Joe and S.H. Zigmond, "CD45 is not Involved in the Processing of Spatial Information Required for Chemotaxis," Journal of Immunology, vol. 147, pp. 243–246, Jul. 1, 1991.

Falk, W., Goodwin, Jr., R.H. and Leonard, E.J. A 48–Well Micro Chemotaxis Assembly for Rapid and Accurate Measurement of Leukocyte Migration,: Journal of Immunological Methods, 33, 1980, pp. 239–247.

Falk, W., Harvath L. and Leonard E.J. "Only the Chemotactic Subpopulation of Human Blood Monocytes Expresses Receptors for the Chemotactic Peptide N–Formylmethionyl–Leucyl–Phenylalanine," Infection and Innunity, vol. 36 No. 2, May 1982, pp. 429–454.

Harvath, L., Falk W. and Leonard E.J. "Rapid Quantitation of Neutrophil Chemotaxis: Use of a Polyvinylpyrrolidone –Free Polycarbonate Membrane in a Multiwell Assembly," Journal of Innunological Methods, 37, 1980. pp. 39–45.

Harvath L., and Leonard E.J. "Two Netrophil Populations in Human Blood With Different Chemtactic Activities: Separation and Chemoattractant Binding," Infection and Immunity, vol. 36, No. 2, May 1982, pp. 443–449.

Richards, K.L. and McCullogh, J., "A Modified Microchamber Method for Chemotaxis and Chemokinesis," Immnological Communications, 13(1), 1984, pp. 49–62.

Stearns, Mark E., "Role of Interluken10 and Transfotming Growth Factor B1 in the Angiogenesis and Mestasis of Human Prostrate Primary Tumor Lines From Orthotopic Implants in Servere Combined Immunodeficiency Mice," Clinical Cancer Research, 5, 1999 pp. 711–720.

* cited by examiner

*Primary Examiner*—Ralph Gitomer
(74) *Attorney, Agent, or Firm*—Shaw Pittman LLP

(57) ABSTRACT

A cell activity assay apparatus ("CAAA") and method using electromagnetic radiation detection beams to measure the activity, e.g., chemotactic response, includes an opaque membrane having a plurality of off-axis pores which prevent experimentally significant amounts of the electromagnetic radiation from traversing the membrane. The membrane is fabricated from opaque films that have been either ablated with substantially off axis excimer laser electromagnetic radiation to form pores, or bombarded by substantially off-axis charged particles and then etched to form pores.

36 Claims, 10 Drawing Sheets

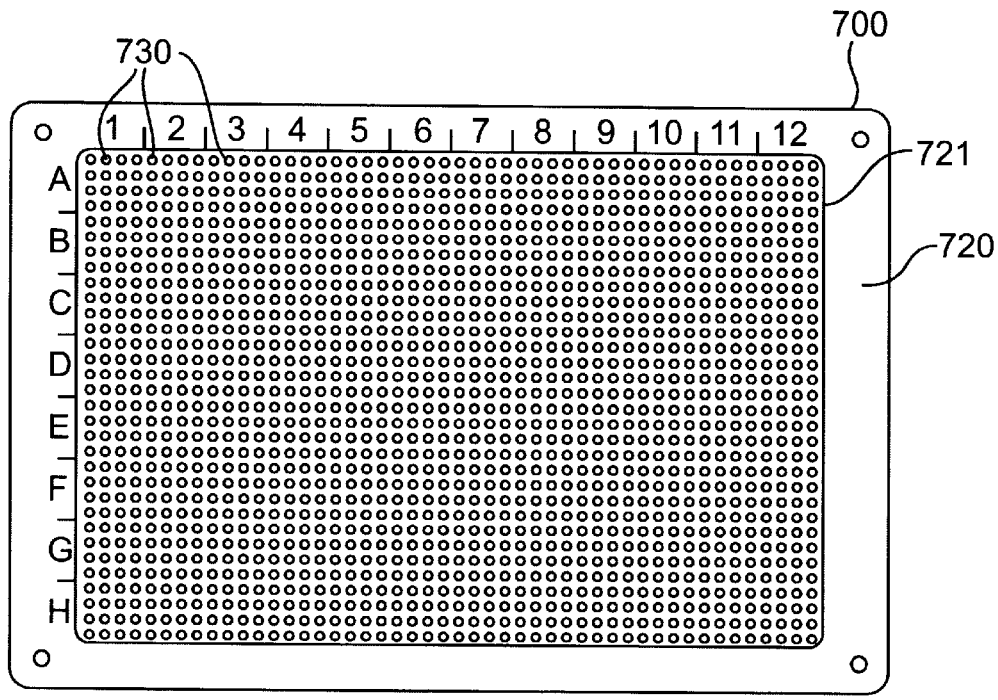
FIG. 7a₁
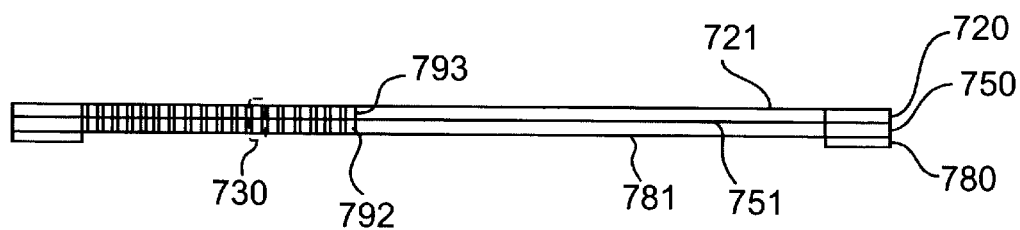
FIG. 7a₂

METHOD FOR USING A CELL ACTIVITY ASSAY APPARATUS

BACKGROUND

1. Field of the Invention

The present invention relates to methods and apparatus for cell activity assay (CAA) investigation of chemotaxis, migration, invasion, angiogenesis, growth, proliferation, differentiation, or interaction of cells in response to various chemical environments.

2. Background of the Invention

Chemotaxis is the directional movement (migration) of biological cells or organisms in response to concentration gradients of chemicals. Invasion is the movement (migration) of cells into or through a barrier. Tumor invasion is such action initiated by cancer cells into or through biological tissue in vivo, or, into or through extra cellular matrix proteins, e.g., collagen or matrigel, into or through barriers made of other substances, in vitro. Angiogenesis is the migration and formation of capillary blood vessels by endothelial cells. Growth is the increase in the size, form, or complexity of cells. Proliferation is growth of cells by cell division. Differentiation is the process by which cells change from a less specialized to a more specialized state usually associated with different functional roles and the expression of new and different traits. Interaction of cells is the alteration of cell behavior such as movement, invasion, angiogenesis, growth, proliferation, or differentiation in response to the presence and action of nearby cells of the same or different type. These activities and similar activities are referred to herein collectively as "cell activity," and the apparatus employed to do the assays is referred to herein as "cell activity assay apparatus."

One kind of single-site conventional cell activity assay apparatus referred to variously in the literature as "chemotaxis chambers," "Boyden chambers," "Boyden chemotaxis chambers," "blind well chambers," or "microchemotaxis chambers," comprises two compartments separated by a membrane, with one or both of the compartments open to air. Multi-site apparatus are referred to as "multi-well chemotaxis chambers," or "multi-well Boyden chambers," and have the same basic site structure but have multiple sites. (See U.S. Pat. Nos. 5,210,021 and 5,302,515) Assays employing this kind of apparatus pipette cells suspended in media into the upper compartments, and pipette chemotactic factors and controls into the bottom compartments. The chemotactic factors can be used in various dilutions to get a dose-response curve. The controls are generally of three kinds: (a) negative, when the same media that is used to suspend the cells is also used below the membrane, (b) chemokinietic, when a cheemotactic factor is placed at the same concentration in the media with the cells and in the well on the opposite side of the membrane, and (c) positive, when a known chemoattractant is placed in the bottom wells. Chemokinetic controls allow the user to distinguish heightened random activity of the cells, due to contact with the chemotactic factor, from directional response in a concentration gradient of that chemotactic factor.

Cell activity assay apparatus can also be used to measure the response of cells of different origins—e.g., immune cells obtained from patients suffering from diseases—to a chemotactic factor of known chemotactic activity. In this case the cells in question are interrogated by both a negative control and a known chemotactic factor to see if the differential response is depressed or normal.

Chemotactic activity is measured by establishing a stable concentration gradient in the cell activity assay apparatus; incubating it for a predetermined time; and then counting, the cells that have migrated through the membrane (or into the membrane). A comparison is then made between the activity of the cells in a concentration gradient of the chemotactic factor being tested, and the activity of the cells in the absence of the concentration gradient.

In one type of cell activity assay apparatus and method, the chemotactic response is measured by physically counting the number of cells on the membrane surface closest to the chamber containing the chemical agent. An example of this type of cell activity assay apparatus is described in U.S. Pat. No. 5,210,021 (Goodwin, Jr.), which is hereby incorporated by reference. One prior art method of obtaining quantitative data is to remove the membrane from the cell activity assay apparatus, remove the cells from the membrane surface closest to the chamber containing the original cell suspension, fix and stain the remaining cells, and then observe and count the stained cells under a microscope. Because of the time and expense associated with examining the entire membrane, only representative areas of the membrane are counted, rendering results less accurate than would otherwise be the case if the entire membrane were examined and counted.

Cell activity assays using a disposable ninety-six well microplate format, for example the ChemoTx™ System (available from Neuro Probe, Inc., Gaithersburg, Md.), is amenable to different methods of quantification of results. The manual staining and counting method described above can be used, but is not recommended due to the time involved. A preferred method is to centrifuge the microplate with filter attached, such that, the cells that have migrated through the filter are deposited onto the bottom of the lower wells. The cells are then stained with MTT, MTS (available from Promega, Madison, Wis.), or similar dye, and then read in a standard automated laboratory densitometric reader (sometimes referred to as an Elisa plate reader).

Another method of obtaining quantitative data with this apparatus is to dye the cells with a fluorescent material, e.g., Calcein AM (available from Molecular Probes, Eugene, Oreg.); centrifuge the migrated cells into the microplate; and count cells with an automatic fluorescence plate reader (e.g., Cytofluor available from PE Biosystems, Foster City, Calif., $Victor^2$ available from EG&G Wallac, Gaithersburg, Md., or fmax available from Molecular Devices, Sunnyvale, Calif.). The automatic plate reader excites the fluorescent dye in the migrated cells with one wavelength of light and reads the light emitted at a second wavelength. Alternatively, the cells that have not migrated are removed from the top of each site. and the plate with framed membrane attached is read in the automatic fluorescent plate reader without spinning the cells into the plate, thereby counting the cells that have fallen off the filter into the lower well as well as those on the bottom of the membrane and in the pores of the membrane.

In another type of chemotaxis apparatus, illustrated by U.S. Pat. No. 5,601,997 (Tchao), the chemotactic response is also measured by labeling the cells with a fluorescent dye, as above. However, in Tchao the membrane is made of film opaque to the excitation and emission wavelengths of the fluorescent dye so that the cells on one side of the membrane can be counted without removing the cells from the opposite side. Tchao's method is an example of a kinetic assay. In such assays, the side of the membrane toward which the cells are migrating is illuminated with the excitation wavelength of the dye, and the cells on that side are periodically counted by measuring the intensity of light emitted in the emission wavelength. This gives the researcher data on the rate at which cells are moving through the membrane. The membrane must be opaque because the researcher cannot remove the cells from the side from which they originated without ending the assay, which makes a kinetic study impossible.

DEFINITIONS & ABREVIATIONS

Abbreviations
1. "Electromagnetic radiation" is herein abbreviated to "ER."
2. "Pore diameter" is herein abbreviated to "pd."
3. "Membrane thickness" is herein abbreviated to "mt."
4. "Radius of curvature" is herein abbreviated to "rc."
5. "High throughput screening" is herein abbreviated to "HTS."
6. "Cell-based high throughput screening" is herein abbreviated to "CBHTS."
7. "Nanometer" is herein abbreviated to "nm."
8. "microliters" is herein abbreviated to "$\mu l$."
9. "micrograms" is herein abbreviated to "$\mu g$."
10. "Coefficient of variation" is herein abbreviated to "CV."
11. "Cell activity assay apparatus" is herein abbreviated to "CAAA"
12. "tcc" herein abbreviates "total count of cells" introduced at a site.
13. "$U_1$" herein abbreviates the quantity of light emitted from the upper volume of a site of a CAAA at the start of an assay. This is proportional to tcc.
14. "$L_1$" herein abbreviates the quantity of light emitted from the lower volume of a site of a CAAA at the start of an assay, known as the background.
15. "$U_2$" herein abbreviates the quantity of light emitted from the upper volume of a site of a CAAA at the end of an assay.
16. "$L_2$" herein abbreviates the quantity of light emitted from the lower volume of a site of a CAAA at the end of an assay.
17. "$CL_2$" herein abbreviates the quantity of light emitted from the lower volume of a site of a CAAA, $L_2$, by subtracting the background $L_1$.
18. "cmc" herein abbreviates "completely migrated cells" which is proportional to $CL_2$.
19. "cmc%" herein abbreviates percent of cmc with respect to the total cells introduced at that site, that is cmc/tcc.
20. "pmc" herein abbreviates "partially migrated cells" which is proportional to $U_1-(CL_2+U_2)$.
21. "pmc%" herein abbreviates percent of cells that partially migrated with respect to the total cells introduced at that site, that is pmc/tcc.
22. "mc" herein abbreviates "migrated cells" which equals cmc+pmc.
23. "mc%" herein abbreviates percent of mc, that is mc/tcc.

Definitions
1. "chamber," "well" or "volume," as used herein with respect to CAAA means the three-dimensional area of the CAAA for holding fluid samples.
2. "off-axis," as used herein with respect to pores in membranes, means pores that are incident to the membranes, when held flat, with an angle of incidence greater than 0° and less than 90°.
3. "Strictly normal," as used herein with respect to a beam of ER and a flat surface, means the entire beam of ER is perpendicular to that surface.
4. "$\beta$-normal," as used herein with respect to ER and a flat surface, means a beam of ER some of which is strictly normal to that surface, and the remainder of which is incident within a range of angles where $\beta$ is the largest such angle and $\beta$<90 degrees. In other words, a $\beta$-normal beam of ER with respect to a surface is a cone of light having $\beta$ as the largest angle of incidence as shown in FIG. 2.
5. "Substantially normal," as used herein with respect to ER and a flat surface, means that the ER is $\beta$-normal to said surface and $\beta$ is less than 15°. (This is in recognition that most detection and quantification systems employed in cell activity assays have detection beams where $\beta$ is less than 15°.)
6. "Detection beam," as used herein with respect to ER, means the ER of an automated reader or detection and quantification system directed at the sites of the apparatus within a specified cone, from a specified distance and from a specified aperture.
7. "$\beta$-normal detection beam," as used herein, means a detection beam using $\beta$-normal ER.
8. "Ideal opaque," as used herein with respect to a film, means film that stops or blocks all ER.
9. "R-opaque," as used herein with respect to film or membrane, means a film or membrane that stops ER in the wavelength range R, where R is specified by a pair of numbers in brackets which delimits a range of ER wavelengths expressed in nanometers.
10. "R-opaque @P%," as used herein with respect to film or membrane, means film or membrane that stops greater than P% of ER in range R, where P is a decimal number between 0 and 100 and represents the percent of ER that is blocked. For example, one film used in embodiments of this invention blocks more than 99.0% of ER in the wavelength range between 400 and 580 nanometers. The same film blocks 99.9% in the ER ranges between 480 and 490, and between 510 and 540 nanometers. This film is herein referred to as "[400–580]-opaque @99.0%" and "[480–490]-opaque @99.9%" and "[510–540]-opaque @99.9%."
11. "Ideal-opaque," as used herein with respect to membranes, means membranes such that (a) the film from which such membranes are made is ideal opaque, (b) the pores of such membranes are straight and parallel, and (c) said pores are positioned or angled such that when the membranes are flat, strictly normal ER cannot pass straight through the pores.
12. "$\beta$-normal-opaque," as used herein with respect to a membranes, means membranes such that no $\beta$-normal ER can pass straight through any pore.
13. "Substantially opaque," as used herein with respect to membranes, means membranes such that no substantially normal ER can pass straight through their pores.
14. "Geometrically R-opaque @P%," as used herein with respect to membranes, means membranes that are (a) made of film that is R-opaque @P%, and (b) no strictly normal ER passes straight through any pore of the membrane. As shown in FIG. 1, the least angle of incidence $\alpha$ of the off-axis pores of such a membrane must satisfy the following equation:

$$\alpha > \phi \text{ where } \phi = \sin^{-1}(pd/mt). \quad (1)$$

15. "$\beta$-normal R-opaque @P%," as used herein with respect to membranes, means (a) the film of the membrane is R-opaque @P%, and (b), no $\beta$-normal ER passes straight through any pore. As shown in FIG. 2, the least angle of incidence $\alpha$ of the off-axis pores of such a membrane must satisfy the following equation:

$$\alpha > (\beta + \theta), \text{ where } \theta = \sin^{-1}([pd \times \cos \beta]/mt). \quad (2)$$

16. "Substantially R-opaque @P%," as used herein with respect to membranes, means membranes that are (a) made of R-opaque film @P%, and (b) allow no substantially normal ER to pass straight through any pore. Thus the least angle of incidence α of the off-axis pores of such a membrane must satisfy equation (2), above, for β<15°.

17. "Substantially perpendicular," as used herein with respect to pores in membranes means pores that are incident to the membranes, when held flat, with an angle of incidence less than 15°.

Note that membranes that are R-opaque @P% are not necessarily substantially R-opaque @P%, β-normal R-opaque @P%, or geometrically R-opaque @P%, since they may have perpendicular pores which allow substantially normal light to pass straight through them. Note that a membrane suitable for cell activity assays will preferably have P greater than 99.0%, and the pore diameter will be greater than 3 microns so that the open area of the membrane formed by the pores will be larger than 2% of the membrane. More specifically, membranes for these applications cannot be R-opaque at 99% if the pores are substantially perpendicular because ER substantially perpendicular to the surface will pass straight through the pores. If, on the other hand, the pores are sufficiently off-axis, and all other aspects remain the same, the membrane can be substantially R-opaque @P%, β-normal R-opaque @P%, and geometrically R-opaque @P%

SUMMARY OF THE INVENTION

The present invention provides CAAA employing membranes and methods for using the CAAA for HTS, CBHTS, and cell based screening, as well as basic research in cell activity. In particular the present invention is a CAAA using a class of membranes that are substantially R-opaque @P%. The present invention also includes the membranes used in the CAAA and methods for their fabrication.

Because the membranes of this invention are substantially R-opaque @P% to the ER wavelengths of the instruments used for detection and quantification with CAAA, detection and counting of cells from one side of the membrane will not be influenced by cells on the opposite side of the membrane or by simultaneous or by subsequent detection and counting of cells on the other side of the membrane. This yields more accurate results than can be obtained with prior art methods. In particular, this allows the use of a method of detection and quantification that eliminates the errors due to both the volumetric inaccuracies of pipetting and the variations in the distribution of cells in the media in which the cells are suspended. This lowers the CV of the assays such that they are appropriate for HTS and CBHTS in drug discovery and development.

Tchao's membrane e is made of film opaque to the wave lengths of excitation and emission of some fluorescent dyes. That is, the Tchao membrane is R-opaque @P%, where R is the range of wavelengths used by the detection and quantification system, and P is the percent of light blocked. The Tchao membrane, however, is specifically required to have substantially perpendicular transverse pores. It is therefore neither a "geometrically R-opaque @P%" membrane, nor a "β-normal R-opaque P%" membrane, where "β" is the largest angle of incidence of light in the detection beam, and "R" is a range of wavelengths of light. It is therefore not a "substantially R-opaque @P%" membrane. ER from detection beams of standard detectors will pass straight through the pores since they are substantially perpendicular. Therefore, with membranes commonly used for cell activity assays which have between 5% and 15% open area (the total area of the pores), the amount of light passing through the pores of the membrane is significant. The transmission of wavelengths normal to the surface of the membrane from the excitation beam will pass through substantially perpendicular pores, and cells on the opposite side of the membrane from the detection beam will be counted if they are over a pore. In other words, light that is β-normal where β is less than 15° will cross the membrane, excite cells that are over pores which will emit light and be counted (since that light will pass back through the substantially perpendicular pores). Thus cells that have not migrated through the membrane will be stimulated to emit ER and will be counted, reducing the accuracy of the results. For kinetic assays, this is not a problem for two reasons. First, the membrane's open area is only between 5% and 15%, and the number of cells that are used for an assay can be set so that they cover only 10% of the membrane. This reduces the number of a cells starting out over pores. Secondly, in a kinetic study, the important parameter is the rate of change, and the fact that cells on the origination side of the membrane are counted when they are over pores means only that the detector will count them much earlier than it would with an opaque membrane made out of the same film with pores that are off axis so that the excitation beam cannot pass directly through them. On the other hand, for assays that measure more than just kinetics or do not measure kinetics, and where the method involves counting all the cells on both sides of the membrane at different points in the assay, as in the methods described below, having substantially perpendicular pores will decrease the accuracy of the assay, and increase the CV significantly.

BRIEF DESCRIPTION OF THE DRAWINGS

FIG. 6b is an enlarged schematic cross-sectional view of a portion of the preferred embodiment of FIG. 6a.

FIGS. 7$a_1$ and 7$a_2$ are a top view and a side view, respectively, of another preferred embodiment of the present invention.

DETAILED DESCRIPTION OF THE INVENTION

Membrane Geometry

Figure 1:
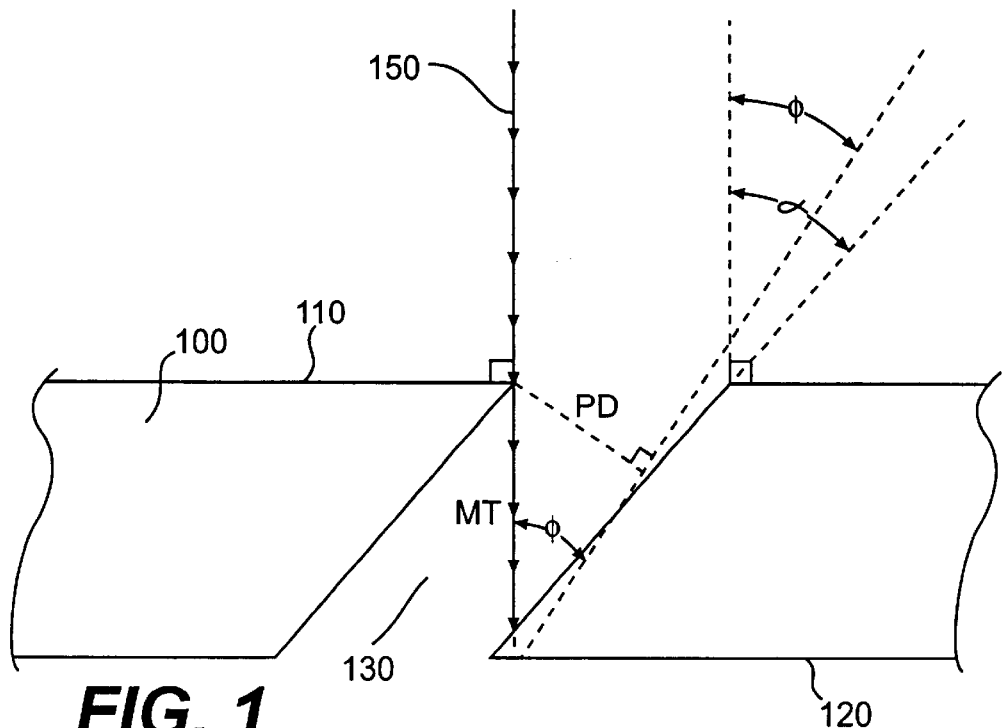
FIG. 1 is a schematic cross-sectional representation of a portion of one of the membranes of the present invention with strictly normal ER.

FIG. 1 is an enlarged cross-sectional view of a portion of an idealized embodiment of a membrane of the present invention drawn with strictly normal ER 150. The membrane 100 of FIG. 1 has a first surface 110, a second surface 120, and a plurality of pores 130. The pores of membrane 100 are off-axis such that the least angle of incidence of any pore is α. The pore 130 has an angle of incidence such that the detection beam cannot travel directly through the pore from the second surface to the first surface of the membrane or vice versa. As shown in FIG. 1, the least angle incidence, α, must be greater than φ, where φ is defined by the equation:

$$\phi=\sin^{-1}(pd/mt) \qquad (1)$$

and where pd is the pore diameter and mt is the membrane thickness. In this case, no ER emitted from a strictly normal detection beam can pass straight through the pores of the membrane.

Figure 2:
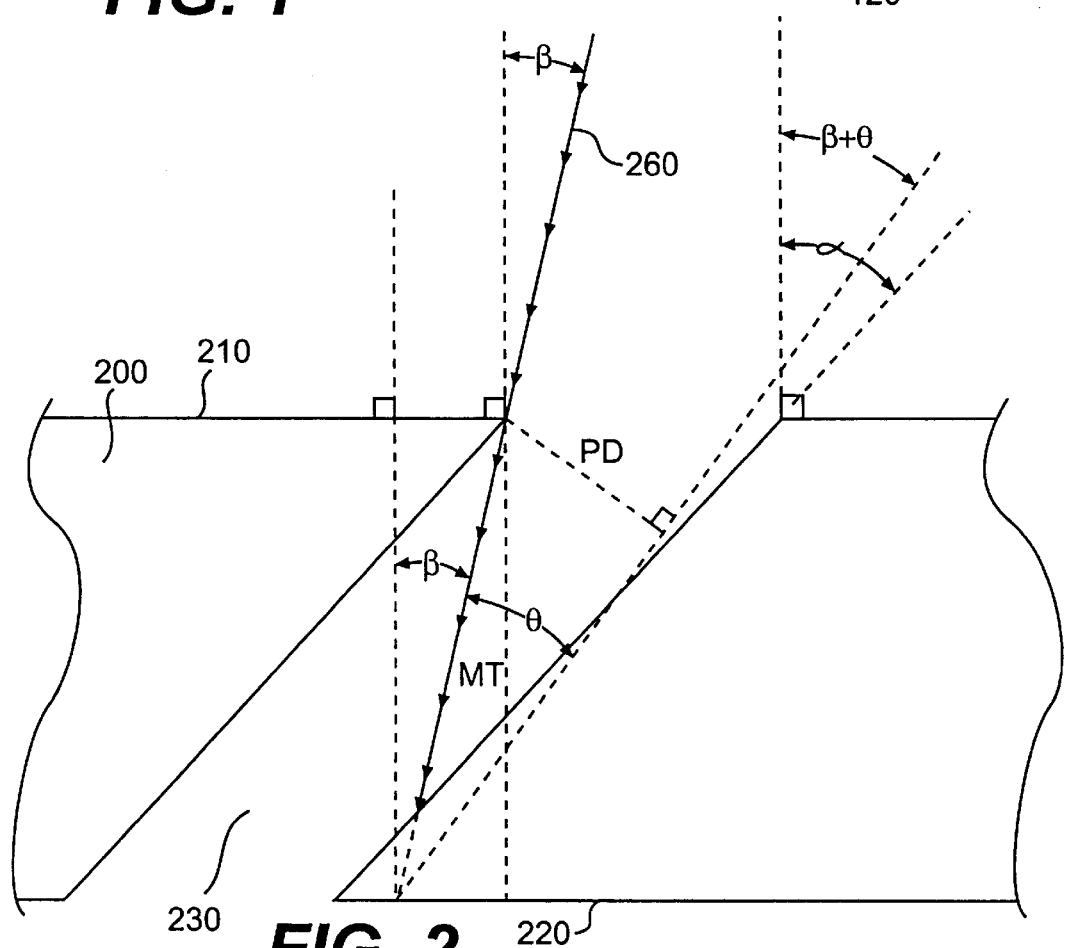
FIG. 2 is a schematic cross-sectional representation of a portion of the membrane of the present invention with β-normal ER.

FIG. 2 is an enlarged cross-sectional schematic view of a portion of the membrane of the present invention. The β-normal opaque membrane 200 has a top surface 210, a bottom surface 220 and a plurality of pores 230. Ray 260 emitted from a β-normal detection beam, having the maximum angle of incidence of the detection beam, β, is drawn in FIG. 2. The pore diameter pd and the membrane thickness mt are as indicated. The angle of a pore of the membrane of least angle of incidence is α. Membrane 200 is β-normal opaque, if and only if:

$$\alpha>(\beta+\theta), \text{ where } \theta=\sin^{-1}([pd\times\cos\beta]/mt). \qquad (2)$$

Figure 3:
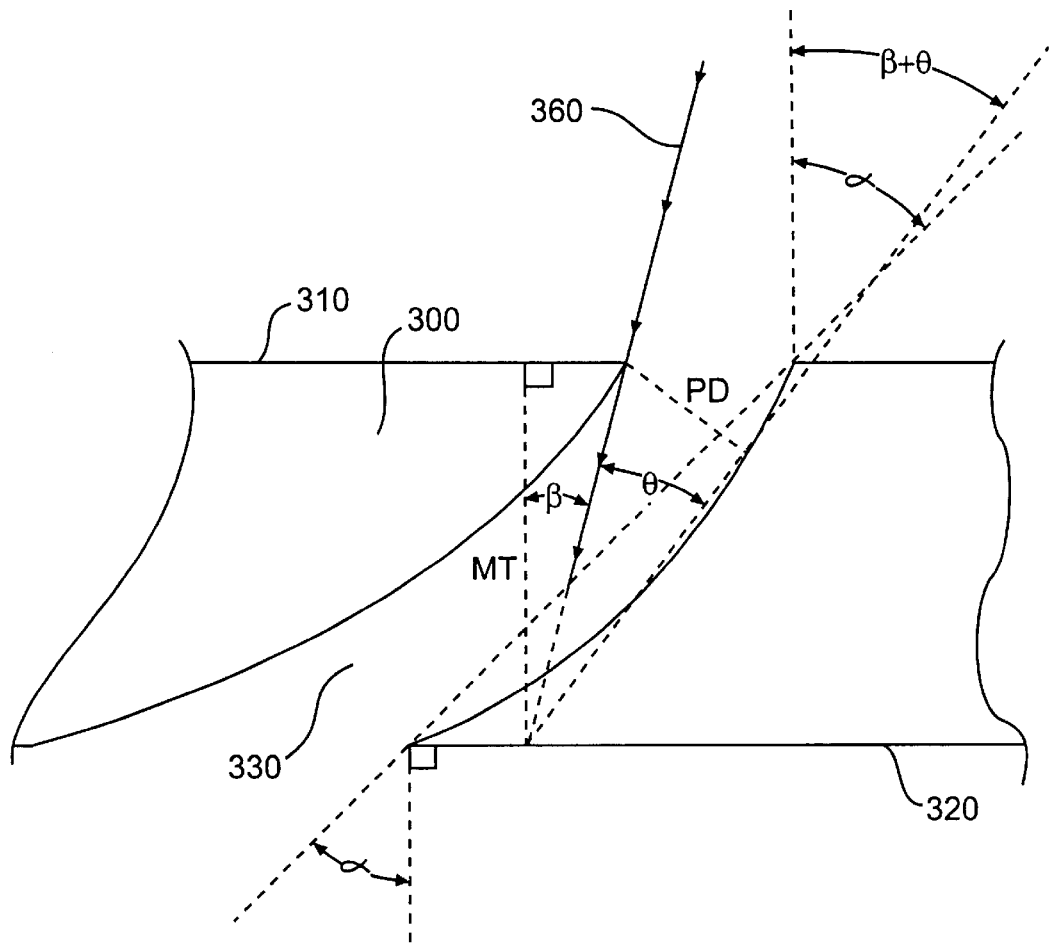
FIG. 3 is a schematic cross-sectional representation of a portion of the membrane of the present invention with curved pores and β-normal ER.

FIG. 3 is an enlarged cross-sectional schematic view of a portion of an embodiment of the membrane of the present invention having curved pores 300. The top surface 310, the bottom surface 320, and a pore 330 are indicated. Ray 360 emitted from a β-normal detection beam, having the maximum angle of incidence of the detection beam, β, is drawn in FIG. 3. The pore diameter pd and the membrane thickness mt are as indicated. The least angle of incidence, α, of a pore of the membrane is determined as indicated in FIG. 3. Membrane 300 is β-normal opaque, if and only if Equation (2) is satisfied:

$$\alpha>(\beta+\theta), \text{ where } \theta=\sin^{-1}([pd\times\cos\beta]/mt). \qquad (2)$$

Membrane Fabrication

Figure 4D:
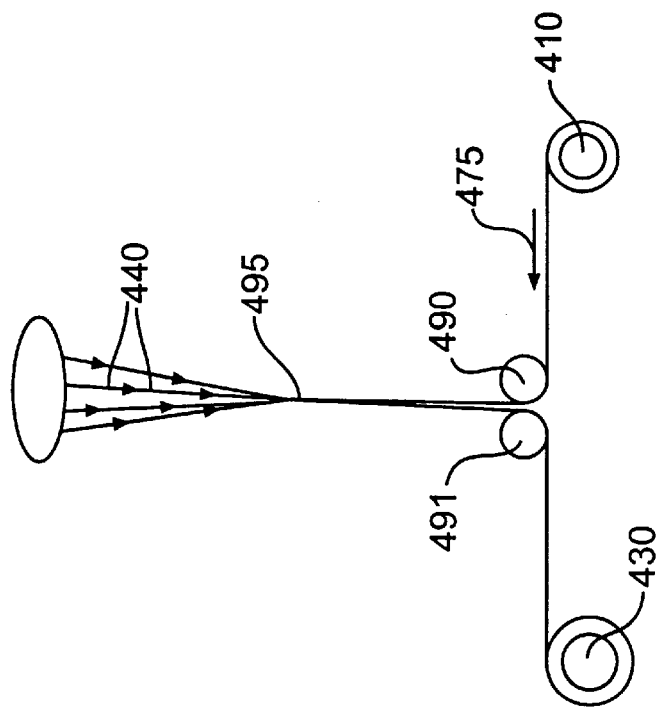
FIG. 4d is a schematic representation of a process for making curved pore membranes of the present invention with an excimer laser.
Figure 4A:
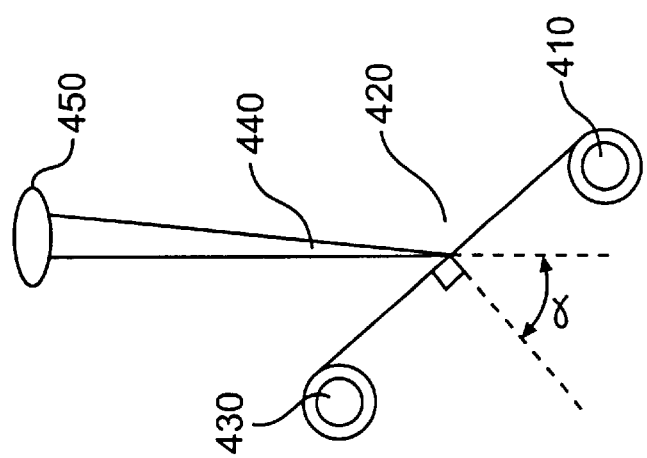
FIG. 4a is a schematic representation of a process for making the membranes of the present invention with a web of film and an excimer laser.

FIG. 4a is a reduced cross-sectional schematic view of an apparatus used in fabrication of embodiments of the membrane of the present invention. The film from which the membrane is manufactured is in the form of a web on a roll called the unwind roll 410, which is unwound and held with a flat section 420 between the unwind roll 410 and a second roll, the rewind roll 430, which contains the fabricated membrane. The flat section of the film 420, between the unwind roll 410 and the rewind roll 430, passes under multiple beams of excimer laser light 440, each beam of which has a diameter slightly smaller than the pores that are being fabricated. How much smaller is determined by the thickness of the film, what the film is made of, and the wavelength of the ER from the laser. Excimer lasers are used because the wavelength of their ER is very short, typically between 200 nm and 400 nm. This allows pores of less than a micron to be made. However, the pore sizes of preferred embodiments of the present invention are 1.0, 2.0, 3.0, 5.0, 8.0, 10.0, 12.0, and 14.0 microns, which are relatively easy to make compared to the submicron pores. The beams of laser light 440 strike the film at angle α, as shown in FIG. 4a. In preferred embodiments, α is between 15° and 70° depending on the particular β-normal opaque membrane required, the membrane thickness, pore diameter and the nature of the cell activity assays in which it is to be employed. In some assays, the shortest possible pores are the most desirable, and in others, longer pores are optimal. For example, if the assay is designed for a minimum incubation period, the pores are preferably short. On the other hand, if maximum sensitivity is paramount, longer pores may be better, since a lower number of negative control cells will pass through the membrane.

The multiple beams of excimer laser ER are created by projecting the output of the laser onto a mask which forms multiple discrete beams, e.g., thousands of beams, which are then focused on the film. The laser ER ablates the film creating straight pores through the material. The power of the laser, the composition of the film material, and its thickness, determines the duration of the ablation. The details are well known to those practiced in the art. One advantage of membrane fabrication with a laser is that the exact position and number of the pores can be controlled. This is advantageous since it lowers the CV of the assays by removing the variation associated with different sites of the cell activity apparatus having different numbers and positions of pores. It also may prove essential as cell-based assays are developed which require smaller and smaller volumes and areas for each site. One preferred embodiment of the present invention employs a microplate sized apparatus (5.030"×3.365" footprint) with 1536 sites of 1 mm diameter. Preferred embodiments of the β-normal opaque membrane employed in this apparatus have pore diameters of 1, 2, 3, 5, 8, 10, 12, or 14 microns, and the thickness ranges between 5 and 50 microns. The pore densities range from 1×10³ to 2×10⁷ pores/cm². The smaller the area of membrane per assay site, the larger the errors become that are associated with pore distribution irregularity. This negatively affects the CV of the whole assay. Consequently, excimer laser fabrication with virtually no variation in the size, number, angle, and position of the pores, is an important advantage.

Figure 4B:
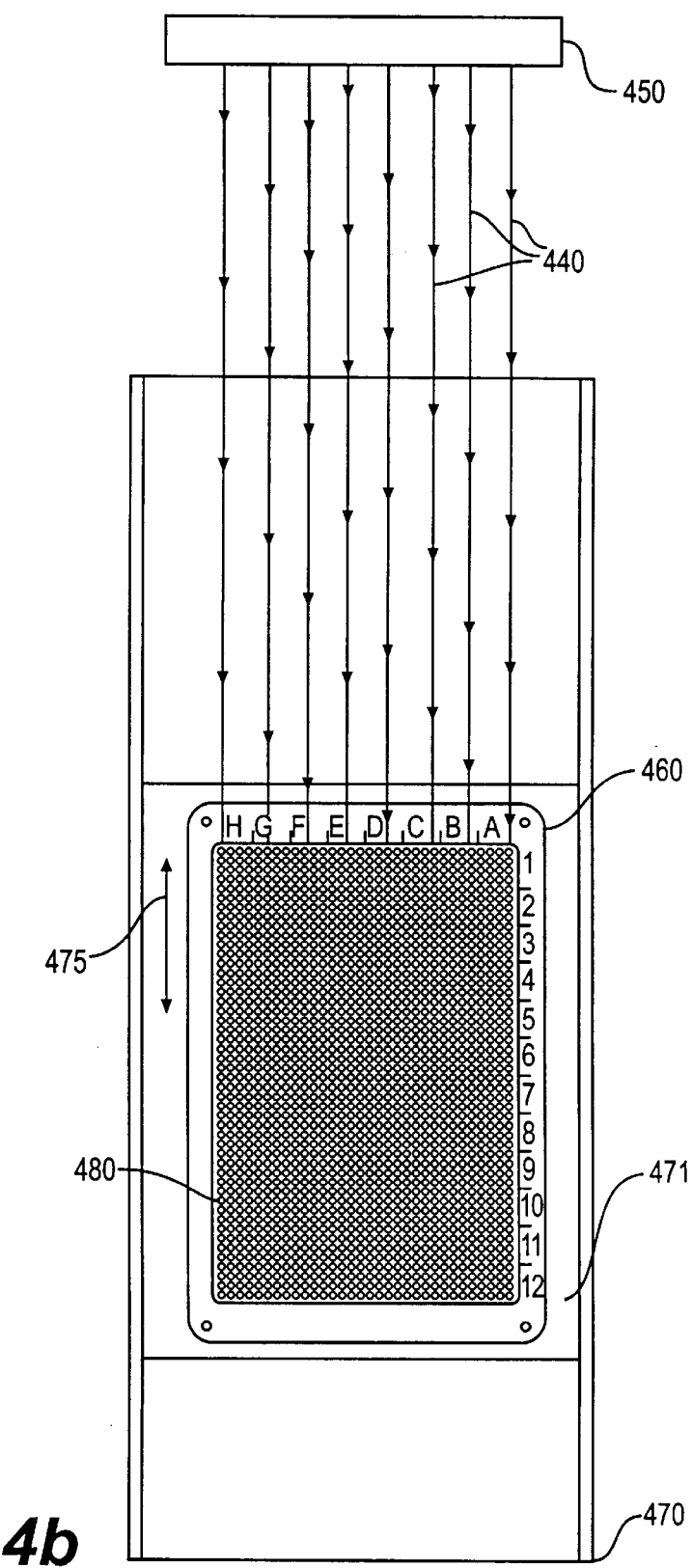
FIG. 4b is a schematic representation of a top view of a fabrication process for making the membranes of the present invention with framed film and an excimer laser.
Figure 4C:
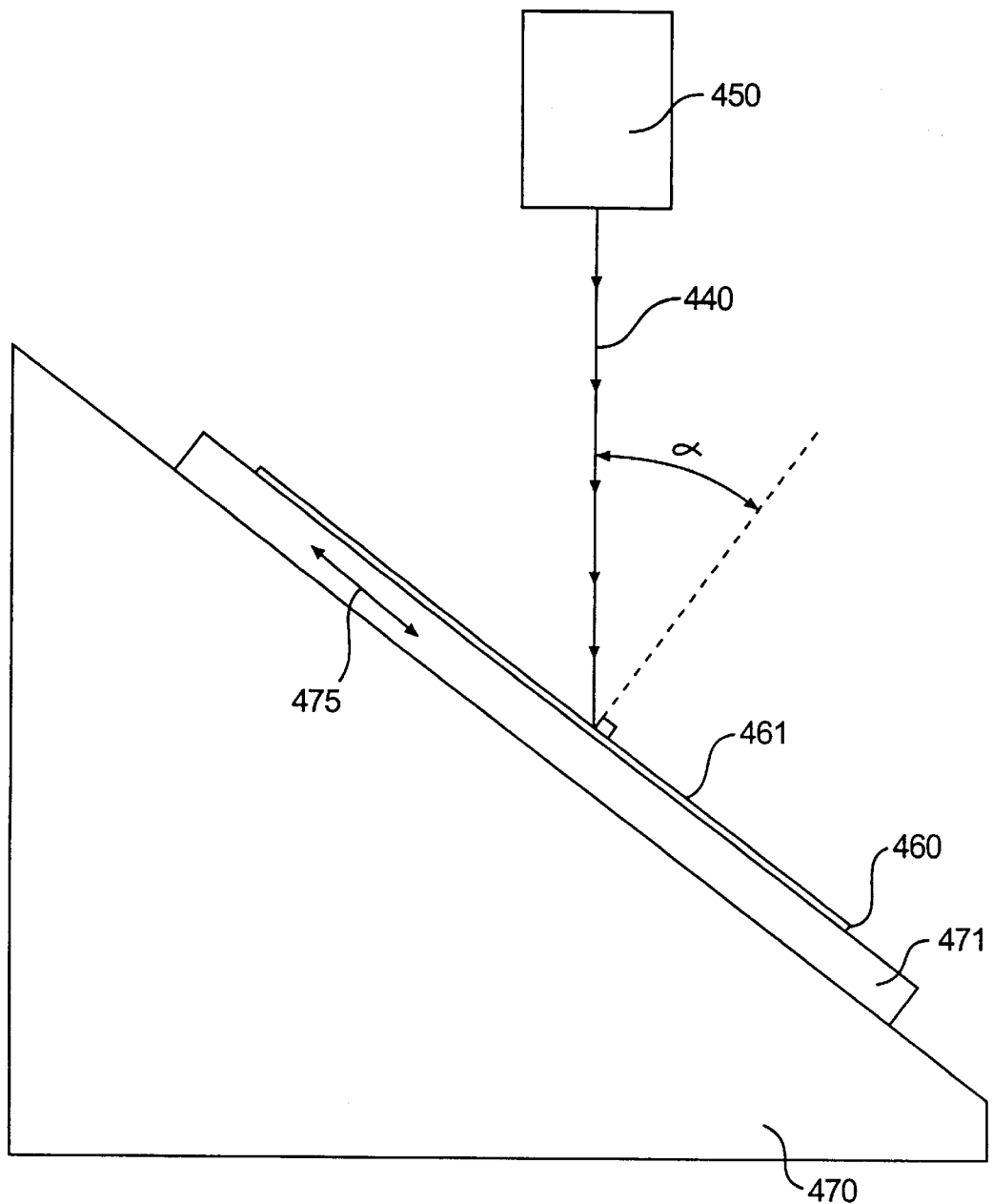
FIG. 4c is a schematic representation of a side view of the fabrication process of FIG. 4b for making the membranes of the present invention with framed film and an excimer laser.

FIG. 4b is a schematic oblique top view and FIG. 4c is a side view of a preferred fabrication method of the membranes of the present invention. With this method, the membranes are constructed from film by ablating pores with a laser apparatus as in FIG. 4a. In this method frames of a CAAA 460 with the film 461 bonded to one side are precisely positioned in an angled jig 470 with a sliding member 471 as shown in FIG. 4c. Multiple laser beams 440, each with a diameter proportional to the diameter of the pores being fabricated, strike the film at an angle of incidence α, as indicated. As described above, Equation (2) must be satisfied to construct a β-normal opaque membrane. That is, $$\alpha>(\beta+\theta), \text{ where } \theta=\sin^{-1}([pd\times\cos\beta]/mt), \qquad (2)$$

where mt is the film thickness, and pd is the pore diameter as shown in FIG. 2. If β<15 degrees the membrane thus manufactured will be substantially opaque. The framed film 461 is moved in the direction indicated by arrow 475 in incremental steps tinder the laser beams 440, preserving the angle α at which the laser beams strike the film. The beams 440 sequentially ablate rows of pores in a pattern defined by a mask (not shown) that forms clusters of discrete beams in the optical path between the source of the laser light (not shown) and a focusing lens system 450 that focuses the clusters of laser beams on the film. In this embodiment of the laser fabrication apparatus, the laser beams 440 are grouped into a pattern 480 corresponding to the sites of the CAAA represented in FIG. 4b by the 32×48 array of 1536 sites. This fabrication technique has several advantages: (a) the number of pores at each site is fixed and (b) said pores can be positioned in any fixed and uniform pattern across the whole framed film 461. This means that site to site variation in CAAA using the framed membrane is practically zero with respect to the membranes. It also means that the application of the hydrophobic mask of some preferred embodiments (described below) is no longer as positionally and dimensionally critical to the uniformity of the sites, and hence to the CV of the assays.

FIG. 4d shows the method of fabrication of the membranes of the present invention from film in which the pores are machined, burned, or ablated with a laser as in FIG. 4a. The film from which the membranes are manufactured is in the form of a web on an unwind roll 410, which is unwound and passes around secondary roller 490 where it changes direction 90 degrees and passes around the fabrication roll 495 of very small diameter. The diameter of fabrication roll 495 is proportional to the radius of curvature (rc) of the pores fabricated with this method: the smaller the diameter of 495 the smaller the rc of the pores. The laser ER strikes the film at a range of angles on a very narrow part of the area of the film where it is bent around the fabrication roller 495. The laser ER ablates straight holes in the bent film, so when the membranes are flat, the pores are bent (see FIG. 3) The membrane web then makes a quarter turn around roll 491 and hence to the rewind roll 430 where it is rewound as fabricated membrane. The film moves in very small incremental steps in the direction indicated by arrow 475, the step increment being determined by the width of the area where the laser ablates the pores in the film. The laser beams 440 sequentially ablate rows of pores, the diameter and pattern of which are defined by a mask (not shown). The range of angles of the pores will be proportional to the diameter of the fabrication roll 495 and the width of the area where the laser beams 440 strike the film.

Figure 5A:
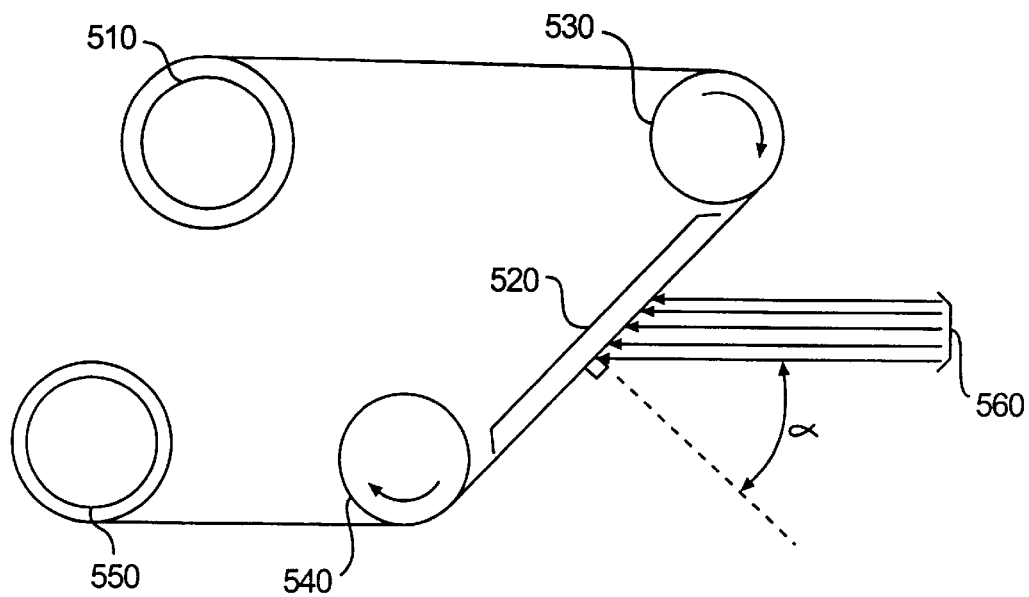
FIG. 5a is a side view schematic representation of a second process for making the membrane of the present invention using cyclotron bombardment (and subsequent etching.)
Figure 5B:
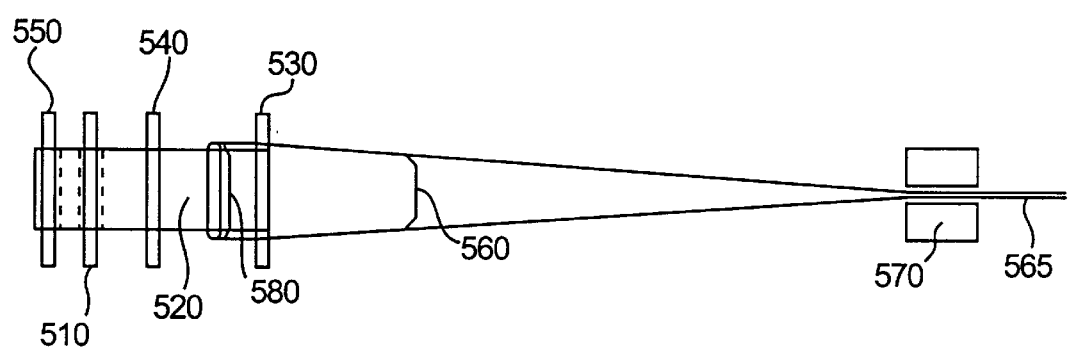
FIG. 5b is a top view schematic representation of the second process for making the membrane of the present invention using cyclotron bombardment.

FIG. 5a is a reduced cross-sectional schematic view of a second kind of apparatus used in fabrication of embodiments of the membranes of the present invention. The film from which the membrane is manufactured is in the form of a web on unwind roll 510, which is unwound and held flat 520 between the intermediate rolls 530 and 540. and then moves to the rewind roll 550, which contains the irradiated membrane. The section of the film held flat and taught 520 between the intermediate rolls 530 and 540 passes under a beam 560 of high energy charged particles emitted by a cyclotron (not shown). The diameter of the high energy particle beam in one preferred embodiment is approximately 6 centimeters, and it is swept back and forth across the web by deflecting it with an electromagnetic field from sweeping magnet 570 as shown in FIG. 5b. The beam sweeps back and forth across the width of the film in a path perpendicular to the line of motion of the web. The beam (or fog of ions) is about 5 meters from sweeping magnet 570 when it penetrates the film. As the beam sweeps back and forth over the width of the film 520, the film moves under it at a steady rate which is determined by the pore density desired for the membrane. As the film passes under the beam, the charged particles pass through it, breaking the molecular bonds of the polymer chains composing the film. The energy of the particles in the beam ranges between 1 and 2 million electron volts and must be sufficient to pass completely through the film at the angle of incidence α of the beam. This angle α is set between 15° and 70°. The optimal angle for a particular β-normal opaque membrane is determined by the membrane thickness, the pore diameter, and the nature of the cell activity assays in which it is to be employed.

In this fabrication technique, the second step of the process is not shown and consists of submersing the irradiated film in an etching bath. This etches pores along the straight paths of broken polymers through the film created by the high energy particles from the cyclotron. The diameter of the pores is determined by the duration of the etching process, and the temperature and concentration of the etching bath. The specifications for this process are well known to those practiced in the art of fabricating track-etch membranes.

Cell Activity Assay Apparatus

Figure 6A:
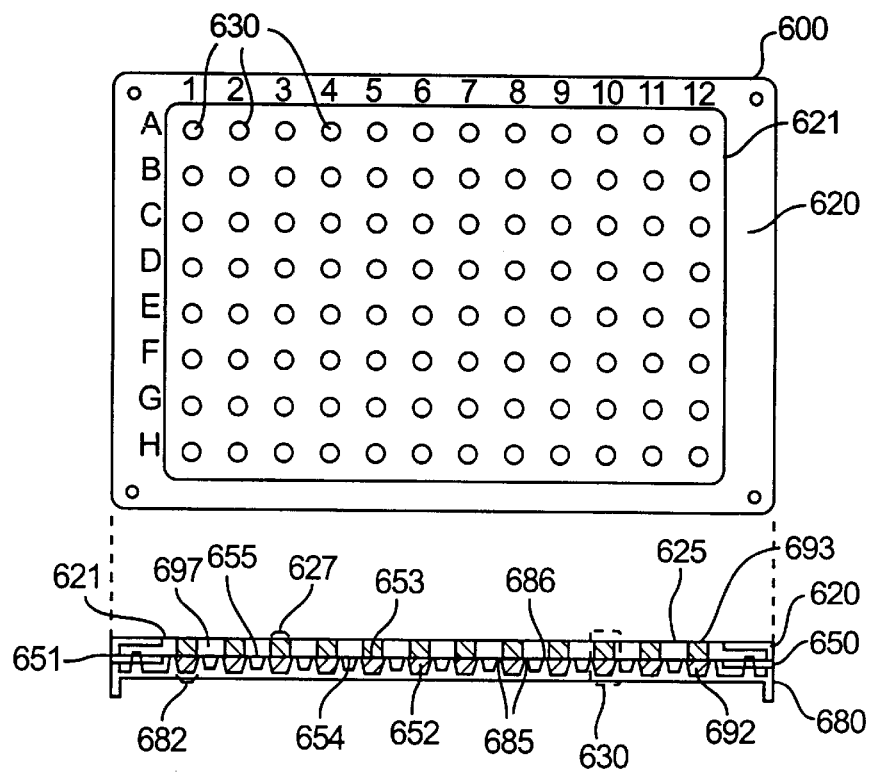
FIG. 6a is a schematic representation of a CAAA comprising a preferred embodiment of the present invention viewed from above.
Figure 6B:
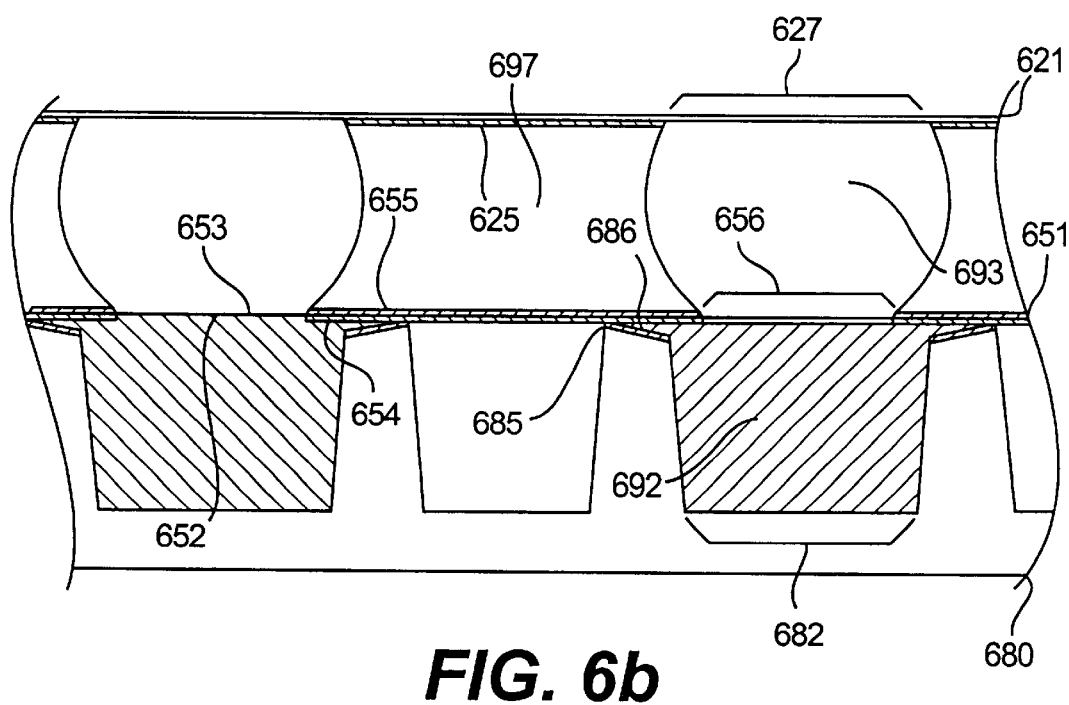
Figure 6C:
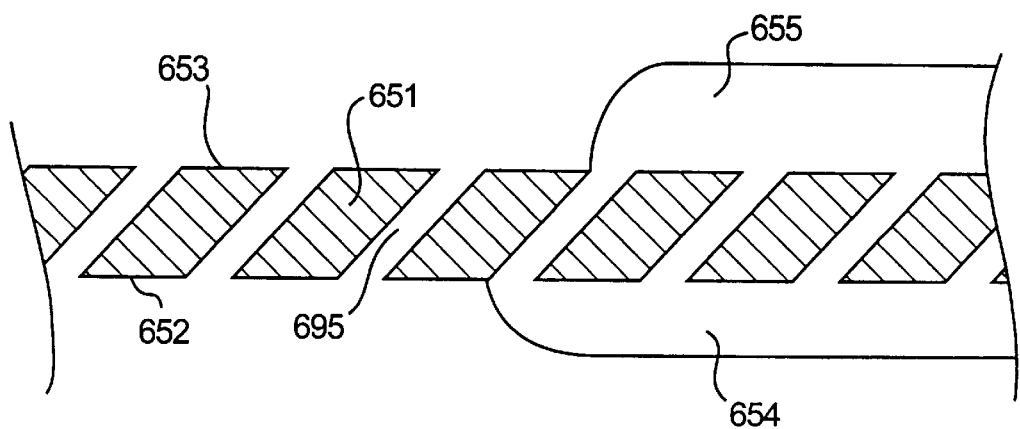
FIG. 6c is a further enlarged schematic cross-sectional view of a portion of the preferred embodiment of FIG. 6a showing the pores of the membrane.

FIGS. 6a–6c are schematic diagrams of an embodiment of the present invention. The multi-site CAAA 600 has a β-normal R-opaque @P% membrane, specifically the substantially R-opaque @P% membrane described above. FIG. 6a is a top and side cross-section view of the whole instrument, and FIGS. 6b and 6c are enlarged cross-section views of portions of the apparatus.

The assay apparatus 600 comprises three rigid parts: an upper part consisting of a transparent film 621 bonded to a rigid frame 620, a middle part consisting of the membrane 651 bonded to a second rigid frame 650, and a bottom part consisting of a transparent injection-molded microplate 680.

The membrane 651 is fabricated from film, which can be made from a variety of materials including plastic, metal, glass, ceramic, organic material, or combinations thereof. The membrane pores 695 (illustrated only in FIG. 6c) can be fabricated in a number of ways, two of which are illustrated and described above. The frame 650 can be plastic, steel, stainless steel, aluminum, or another suitable material. The frame must be rigid enough to keep the membrane, and any grids, coatings, or site-delimiting devices attached thereto, substantially flat. The membrane can be attached to the frame by any suitable fastening means, including glue, heat seals, ultrasonic seals, or mechanical means.

FIG. 6a shows the ninety six (96) assay sites 630 of CAAA 600 arranged in an 8×12 array. Each assay site 630 comprises a discrete, delimited area 656 of membrane 651, along with two three-dimensional compartments (wells)— the upper volume or well 693, above the membrane 651, and the lower volume or well 692, in the microplate 680 below the membrane 651.

The film 621 delimits the top of each upper volume 693 and creates optically advantageous flat surfaces, which minimize reflection and refraction of ER from detection beams and ER emitted from the upper well of the test sites 630. An opaque mask 625, affixed to the bottom surface of film 621, surrounds and separates the transparent spots 627 at the tops of the assay sites 630. This mask is also hydrophobic and circumscribes the top perimeters of the upper volumes 693.

FIG. 6c shows a greatly enlarged view of a section of the membrane 651, which, with the frame 650, forms the middle part of the CAAA 600. FIG. 6c illustrates the off-axis pores 695 of substantially R-opaque @P% membrane 651. This figure also shows a membrane section at the edge of an assay site 630 and illustrates the two hydrophobic masks that are affixed to the membrane 651, one (655) on the top surface 653 and one (654) on the bottom surface 652. Hydrophobic mask 655 delimits the bottom perimeter of the upper volume of site 630, and circumscribes the membrane area 656 where cell activity can occur across the membrane. Hydrophobic mask 654 helps circumscribe the top surface of the lower volume, as described below.

During an assay, the upper volume (upper well) 693 and lower volume (lower well) 692 of each site 630 are filled with fluid solutions containing chemical compounds and/or biological cells in suspension as shown by the shaded areas in FIG. 6b and the cross-section view of FIG. 6a. Surface tension of the fluid in each upper volume 693, along with the pair of hydrophobic masks 625 and 655, confine upper-volume fluid and create air space 697 surrounding and isolating the upper volumes. Hydrophobic coating 686, affixed to the rim 685 of the lower volume 692, forms a shield seal with the hydrophobic mask 654 on the under side 652 of membrane 651. The membrane 651 is positioned and held on top of and against the rims 685 of the lower well 692, which confines the lower-volume fluid. The flat transparent bottoms 682 of the wells in the microplate 680 are optically advantageous surfaces through which light can pass into and out of the lower volumes 692.

FIGS. $7a_1$ and $7a_2$ show the top view and a side view, respectively, of a CAAA 700 having one thousand five hundred and thirty six (1536) assay sites. In this embodiment the assay sites 730 are arranged in a 32×48 array within the footprint of a standard microplate (5.030"×3.365"). The apparatus 700 is composed of three rigid parts: an upper rigid frame 720, a middle rigid frame 750 and a lower rigid frame 780. The upper rigid frame 720 is bonded to a transparent film 721. The middle rigid frame 750 is bonded to substantially R-opaque @P% membrane 751. The lower rigid frame 780 is bonded to transparent film 781. Each of the assay sites 730 has an upper volume 793 and a lower volume 792, as shown in FIG. 7b.

Figure 7B:
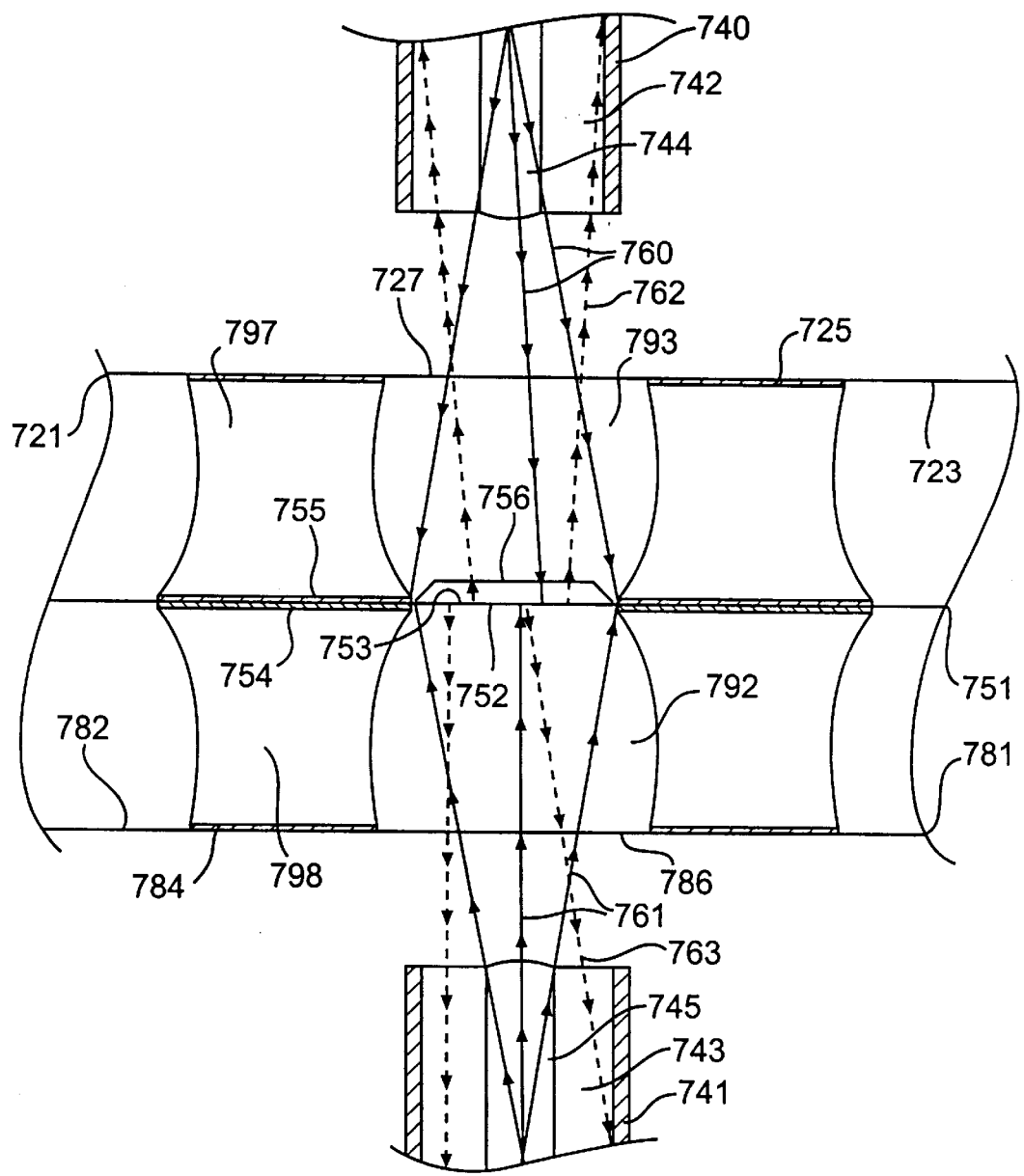
FIG. 7b is an enlarged schematic cross-sectional view of a part of the preferred embodiment of the present invention of FIGS. 7$a_1$ and 7$a_2$.

FIG. 7b is a cross-sectional, enlarged, schematic view of a portion of CAAA 700. The upper film 721 has a hydrophobic mask 725 bonded to its bottom surface 723. The membrane 751 has a top hydrophobic mask 755 bonded to its top surface 753, and a bottom hydrophobic mask 754 bonded to its bottom surface 752. The lower film 781 has a top surface 782 with a hydrophobic mask 784 bonded to it.

Each assay site 730 consists of the following elements: the transparent area 727 of upper film 721 and hydrophobic mask 725 on lower surface 723 surrounding transparent area 727, the open area 756 of membrane 751 and hydrophobic mask 755 on the top surface 753 of membrane 751 surrounding 756, and hydrophobic mask 754 on bottom surface 752 of the membrane 751, the transparent area 786 of the lower film 781, the hydrophobic mask 784 on the top surface 782 of the lower film 781, and the upper volume 793 and the lower volume 792. The upper air space 797 and lower air space 798 surround and separate each of the sites. In this embodiment, the volumes 793 and 792 are between 0.5 μl and 2.5 μl, and the distances between the centers of sites 730 is 2.25 mm.

Hydrophobic masks 725 and 784 are opaque and surround transparent areas of the top film 727 and bottom film 786, respectively, that are directly above and below each assay site. ER from the detection beams 760 and 761 and the ER 762 and 763 emitted by the fluorescent dye in the upper and lower volumes pass in and out through upper transparent area 727 and lower transparent area 786, respectively. The detector/quantification apparatus above the upper film 721 is composed of a housing 740, a fiber optic bundle 742 for collecting emitted ER 762 from the top volume 793 and top surface 753 of the site 730, and another optical conduit 744 for delivering the excitation ER 760 to the upper volume 793 and upper surface 753 of the membrane of the sites 730. The detector/quantification apparatus below the lower film 781 is composed of a housing 741, a fiber optic bundle 743 for collecting emitted ER 763 from the bottom volume 792 of the site 730, and another optical conduit 745 for delivering the excitation ER 761 to the lower volume 792 and lower surface 752 of the membrane of the site 730.

The interfaces between the three rigid frames 780, 750, and 720, can be either sealed to gas exchange or not as required by the assay. In most cell-based assays, airflow needs to be minimized to prevent excessive evaporation, without overly inhibiting diffusion of oxygen and carbon dioxide. This can be accomplished in a number of ways including: positioning a thin layer of open cell foam between the frames, providing multiple small channels between the frames, providing film material for 721 and/or 781 with sufficient gas exchange rates, providing microscopic holes in 721 and/or 781 between the test sites, or providing enough microscopic pores in 721 and/or 781 at the test sites for sufficient gas exchange.

The materials from which suitable films can be made for the fabrication of opaque membranes include plastics, organics, metals, glass, ceramics and combinations thereof. In preferred embodiments of the opaque membrane of the present invention, polyester film is used with various dyes that make it opaque at various wavelength ranges that match fluorescent excitation and emission bands of the various dyes used to tag or label the cells used in the cell activity assays. The embodiments, described above, manufactured with the cyclotron bombardment and etching technology require materials that can be etched. Polyester and polycarbonate have excellent etching characteristics and are widely used. Polyester is preferred because it is easy to introduce dye into the film after it is initially fabricated. Polycarbonate film is now fabricated with dye incorporated into the basic film, but at this time the other characteristics of this film, in particular the uniformity of its thickness, make it a poor candidate.

Coating or depositing metallic layers on plastic films and/or membranes is another method of making the membranes opaque. There are advantages and disadvantages to this fabrication technique. For example, with a dyed substantially opaque membrane, some light passes through the pores via reflections within the pores. The amount of light which passes through, however, is insignificant and is not a practical problem since standard detection/quantification systems used for cell activity assays are not sensitive enough to measure it. If the membrane is coated with metallic atoms, however, the interior surfaces of the pores can be extremely reflective. This is counter-productive to the goal of fabricating a substantially R-opaque @P% membrane where P is above 99.9%. Furthermore, the deposited coating must not interfere or affect the activity of the cells used in the assays.

Methods of Using Cell Assay Apparatus

In one method for using the embodiment of the invention, shown schematically in FIGS. 6a–6c above, cells to be interrogated are positioned on one side of the membrane and solutions to be assayed for their influence on cell activity are positioned directly opposite on the other side of the membrane. The preferred membrane of this embodiment is substantially R-opaque @P%, where R is 400 nm–580 nm and P% is 99.9% and the membrane thickness is 31 microns, the pore diameter is 8 microns, the range of angles of incidence of the off axis pores is between 44° and 46°. When using such a CAAA with 485 nm ER for excitation and 530 nm detector/quantification systems for ER emitted by the cells in the sites, the contribution of the cells on the opposite side of the membrane from the excitation/detection/quantification system is less than 0.0005% of the count at any site. The membrane could have a pore density between $1 \times 10^3$ and $1 \times 10^9$ pores/cm$^2$, a thickness between 1 and 1000 microns, and pores with angle of incidence between about 15° and 70°.

Several methods using CAAA 600 or similar apparatus are described in more detail below.

Method I

Method I comprises the following steps:

1. About eighty-four of the lower volumes (wells) 692 are filled with 30 μl of test solutions, i.e., positive controls, negative controls, or unknowns.
2. The remainder—about one row of lower plate 680—are filled with 25 μl of cell suspension in a serial dilution down to a cell concentration at or just below the lower sensitivity limit of the detection/quantification system. This provides a standard with which to compensate for reader error when the lower volume of the test sites are read.
3. The rigid framed membrane 650/651 is positioned and attached to the microplate.
4. About 25 μl of cell suspension is applied to the upper surfaces 653 of membrane 651 in about eighty-four of the upper volumes 693 of the test sites. 25 μl of the same cell suspension in a serial dilution is then added to the remaining, upper sites as in step 2. This provides a standard with which to compensate for reader error when the upper volume of the test sites are read.
5. The lid 620/621 is positioned and attached to the CAAA.
6. An automatic fluorescence reader is used to read assembled CAAA 600 and determine values for $U_1$ and $L_1$ at each site. The data are stored in memory for later comparison, compensation, and computation.
7. CAAA 600 is incubated at the appropriate temperature and humidity (e.g., in human CAA, 37° C. and 98% relative humidity is generally appropriate), and the appropriate interval of time for the particular cell activity assay. This period is usually between 15 minutes and 48 hours. The optimal incubation period is determined by doing kinetics or a sequence of experiments with different incubation times, and then selecting the incubation period that gives the optimal result. In a cell activity assay this usually means the result where the difference between counts at the negative control sites, and at the positive control sites is maximized. In HTS, however, where the longer the time of incubation, the more expensive the assay, the optimum incubation might be much shorter. It might be the shortest time required to determine whether a significant difference exists between negative control sites, positive control sites and sites with the compounds being screened.
8. CAAA 600 is removed from the incubator and read a second time as described in step (6) and the values $U_2$ and $L_2$ for each site and the data are stored in the computer memory.
9. The computer calculates the cmc, cmc%, pmc, pmc%, mc, and mc% from the data collected in steps 6 and 8.

The computer can also compensate for the errors in the detection/quantification system by using the data collected from the row of sites with the serial dilutions of the cell suspension. It then calculates the averages of these above-mentioned figures for each set of replicate sites (usually between 2 and 4) and compiles the results of the whole assay comparing positive site sets, negative site sets and unknown site sets. It also calculates the CV for the assay. The calculated results are then available for further analysis.

Method II

Method II comprises the same steps as Method I, in addition to the following step, step 7a, performed after step 7:

7a. Kill all the cells in the upper wells, or kill all the cells in the apparatus, by (1) irradiating them with short wavelength ER, e.g., 254 nm, (2) removing the lid 620/621 and replacing it with another lid with about 10 μl of a solution on each site on the bottom surface 623 of the film 621, that rapidly kills the cells, or (3) some equivalent method.

Method III

Method III comprises the same steps as Method I, in addition to the following step, step 7b, performed after step 7:

7b. Immobilize all the cells in the upper wells or in the entire apparatus by; (1) freezing the cells (usually accomplished by freezing the entire apparatus), (2) rapidly lowering the temperature of the cells (or apparatus) to between 0° C. and 4° C., (3) removing the lid 620/621 and replacing it with another lid with solutions affixed to all the sites on the lower surface of film 621 that immobilize the cells, e.g., 4 millimolar EDTA, or (4) some equivalent method.

Methods II and III are preferred over Method I in cases where the cell activity is so rapid that the accuracy of the results will be compromised by the difference in elapsed time the cells are active at different test sites. This can be very significant if the incubation time is short, e.g., less than thirty minutes, and the detection/quantification time is long, e.g., ten minutes. With the large number of sites used for HTS and ultra-HTS (e.g., 1536 and 3456 sites) the cells must be killed or immobilized for accurate results.

Methods IV through VI

Method IV is a simplified version of Method I. In this method, all of the steps of method I are performed, with the exception of step (6). Thus, in this simplified version, the readings of the emissions from the upper and lower wells are obtained only once.

Method V is a simplified version of Method II and Method VI is a simplified version of Method III. That is, as described above, the readings of step (6) are not performed.

These simplified Methods IV through VI will not yield nearly as much data, and the information extracted from the data will not be as rich or sensitive, but it may be sufficient in some screening contexts. The advantages of these simplified methods are that they are faster and less expensive than Methods I through III.

Method VII

Method VII is essentially a class of methods. Method VII comprises all of the Methods I through VI, using an apparatus having a membrane that is R-opaque @P%, but not substantially R-opaque @P%. That is, the membrane used in this class of methods has pores that allow substantially normal ER, such as that used by state-of-the-art detection/quantification systems, to pass straight through the membrane. This will yield adequate results in some CBHTS contexts, although the sensitivity will be lower, particularly in comparison with Methods I through III.

Method VIII

Method VIII is another class of methods. These methods use a CAAA such as that disclosed above and illustrated in FIGS. $7a_1$, $7a_2$, $7b$, and $7c$. In these methods the first five steps of Method I through VII are modified as follows:

1a. The various control solutions, positive and negative, and test solutions, e.g., chemotactic factors, are prepared cold. The solutions contain a sufficient proportion of collagen, gelatin, fibernectin, lamanin, or other appropriate gel-forming material compatible with the cells of the assay, to gel at temperatures of about 20° C. to 40° C. The solutions do not gel when held between about 4° C. and 10° C., so they can be prepared in advance and stored at 4° C. When they reach between about 20° C. and 37° C., they gel. Temperature, pH, and concentration of the gelling agents determine the amount of time required to gel. These parameters can be manipulated for convenience within certain limits. For example, approximately 100 µg of Type I collagen in one ml of DMEM buffer at pH 7.2 is a good medium for many cell activity assays. (See M. E. Stearns et. al, *Clinical Cancer Research,* Vol. 5, March 1999). Identical volumes between 0.5 µl and 2.5 µl of cold solutions containing gel-producing compounds mixed with the compounds to be tested, e.g., positive controls (known chemotactic factors), negative controls with no additional compounds, and unknowns, are pipetted onto the top surface 782 of the bottom film 781 surrounded by hydrophobic mask 784 that defines the bottom of the lower volume of the test sites 730 with a pipetting robot (e.g., Model C-300 or Model C-400, Cyberlab, Inc., Brookfield, Conn.). About 1500 sites of the available 1536 are filled. The droplets of solution adhere to the film 781 and rise between 1.0 mm and 1.7 mm above the top surface 782. The hydrophobic masks visually define the locations of the cell activity test sites and prevent the lateral movement of the test solutions.

2a. The remainder of the test sites are filled with a serial dilution of the cell suspension, but in this case the same volume is used as in step (1a). Other kinds of control and calibration solutions, e.g., fluorescent dyes, can also be placed at various positions on the apparatus to facilitate detection of errors in the various components of the system and to enable compensation for such errors.

3a. The rigid framed membrane 750/751 is then positioned over and attached to the lower framed film 780/781. The alignment and attachment hardware or bonding agents fix the lower and middle components of the apparatus together. The final distance between the membrane and the bottom film is determined by the thickness of the portion of the frames between the top surface of the lower film 782 and the bottom surface of the membrane, 752 and is such that the solutions on the lower film contact and wet the lower surface 752 of the membrane 751. If volumes at the low end of the range are desired, this distance is decreased, and vice versa.

3b. These two components 780 and 750 now attached together are set aside or placed in an incubator for a period between 10 and 90 minutes to allow the solutions to gel.

4a. Between 0.5 µl and 2.5 µl of the cell suspension is then pipetted onto about 1500 sites on the top surface 753 of the membrane 751. In this case, however, the sites with the serial dilutions of the cell suspension and the other sites with control and calibration solutions have no cell suspension solutions applied. This is because in CAAA 700, the solutions at these sites in the lower wells make contact with the bottom side 754 of the membrane, which is not the case with CAAA 600.

5a. The lid 721/720 is then positioned over the framed membrane 750/751 and placed down on the two lower components where it is attached by the attachment hardware or bonding agent. The lower surface 723 of the upper film 721 makes contact with approximately 1500 volumes of cell suspension, and the three rigid components of the apparatus 720, 750, and 780 become a unit 700.

At this point in the procedure, any of Methods I through VIII commencing with step (6)(as described above) can be followed, making the necessary changes in the procedure required by the changes in the hardware. For example, the detector beams of the automatic fluorescent reader have to be smaller, as would the optical collection system that collects and measures the amount of light emitted from the upper and lower volumes of the sites.

The methods described above, using apparatus 600 or 700 or similar apparatus, allow the detection and quantification at each site of (a) the number of cells pipetted, (b) the number of cells that have migrated through the membrane, (c) the number that have not migrated, (d) the number that have migrated into the membrane but have not passed through , and (e) the total number that have migrated. From this data, the percent of the cells that have migrated at any site can be calculated as well as the percent of cells that have passed through the membrane at that site. Since these results are calculated independently for each site, both the errors associated with pipetting (variations in volume) and the errors associated with the uneven distribution of cells in a unit volume are eliminated.

If the substantially R-opaque @P% membrane used in apparatus 600 or 700, was fabricated according to the method disclosed in FIG. 4*b* and FIG. 4*c,* further reduction in the CV is achieved due to complete uniformity in the number of pores from site to site.

When Method VIII is used with CAAA that employ R-opaque @P% membrane that is not substantially R-opaque @P%, the results will be adequate in some CBHTS contexts. These include assays where it is desirable to use (a) very low pore densities, (b) large pore diameters, (c) thin membranes, and (d) low cell densities. The system must also have very low background fluorescence and the detection/quantification system must be very sensitive. In these contexts, the detection system detects cells when they migrate over pores. New detection instruments are being developed e.g., Cellomics (Pittsburgh, Pa.) which have high resolution optical systems that may accomplish this. Migration of cells in this context would not be measured by how many cells passed through the membrane, but how many migrated over the top of a pore. Such assays are rare and expensive. When this CBHTS context exists, the methods used would most likely be designed to acquire data about the kinetics of cell activity, and these methods are different from the ones described here.

All of the above methods can be modified so that the cells are introduced into the lower well of the CAAA. For example, in Method VIII, the cells can be suspended in an ungelled gel solution, as described above, and applied to the sites on the bottom side of the membrane when it is inverted. The inverted lower framed film is then positioned over and attached to the inverted framed membrane. When the solutions gel, the apparatus is inverted and test solutions and controls are applied to the top sites of the membrane, and then the upper framed film is positioned and attached. The cells now migrate up through the filter. Similar results can be achieved with CAAA similar to 600, making the changes necessary to accommodate the differences in the apparatus.

Many variations and modifications of the embodiments described herein will be obvious to one of ordinary skill in the art in light of the above disclosure. For example, in an alternative CAAA, each site is a well provided with an insert which divides the well into an upper chamber and a lower chamber. In some such CAAA the inserts are attached together in the form of a plate. The insert incorporates the membrane of the present invention.

As another example, in some cases, chemical interactions between the cell sample and a chemical in the sample solution or chemical introduced into the solution after cell movement through the membrane creates light which is detected without introducing an ER beam. In such cases, the pores would be angled to block transmission of ER that may be emitted by non-migrated cells if the chemical diffuses into the chamber on the opposite side of the membrane. Further, the present invention could also encompass assays in which the sample is not necessarily in a liquid medium but, for example, may be carried by a gas medium so long as the membrane is substantially opaque to the ER wavelengths introduced and detected.

The foregoing disclosure of embodiments and methods of the present invention has been presented for purposes of illustration and description. It is not intended to be exhaustive of to limit the invention to the precise forms disclosed. The scope of the invention is to be defined only by the claims appended hereto, and by their equivalents.

What I claim is:

1. A method for assaying cell activity, comprising the steps of:
   (a) providing a cell activity assay apparatus having a plurality of test sites,
      wherein each test site of the plurality of test sites has a membrane that has a first surface and a second surface,
      wherein the membrane separates a first fluid sample, containing a plurality of cells in contact with the first surface of the membrane, from a second fluid sample in contact with the second surface of the membrane, and
      wherein the membrane is made of opaque film and has membrane pores such that cells may migrate through the membrane pores but electromagnetic radiation substantially normal to the first surface and the second surface of the membrane does not pass straight through the membrane pores;
   (b) incubating the cell activity assay apparatus;
   (c) directing a first beam of electromagnetic radiation having a first wavelength toward the first surface of the membrane through the first fluid sample, at each site of the plurality of test sites;
   (d) measuring a first quantity ($U_2$) of electromagnetic radiation having a second wavelength thereby emitted, at each site of the plurality of test sites;
   (e) directing a second beam of electromagnetic radiation having a first wavelength toward the second surface of the membrane through the second fluid sample, at each site of the plurality of test sites;
   (f) measuring a second quantity ($L_2$) of electromagnetic radiation having a second wavelength thereby emitted, at each site of the plurality of test sites; and
   (g) at each site of the plurality of test sites, determining the percentage of cells that have migrated through the membrane pores,
      wherein the percentage is proportional to $((L_2)/(U_2+L_2))$, and
      wherein the percentage corresponds to the cell activity.

2. The method of claim 1, further comprising the steps of:
   (h) determining, at a particular test site of the plurality of test sites,
      the number of cells (tcc) in the plurality of cells of the first fluid sample before the step of incubating,
      the number of cells (umc) present on the first surface of the membrane after incubating, wherein umc is proportional to $U_2$,
      the number of cells (cmc) that have migrated through the membrane pores, wherein cmc is proportional to $L_2$, and
      the number of cells (pmc) that have migrated into the membrane pores but have not passed through the membrane pores, wherein pmc=tcc−(umc+cmc); and
   (i) calculating the percentage of migrated cells (mc%) at the particular test site,
   wherein mc%=((cmc+pmc)/(cmc+pmc+umc)).

3. The method of claim 2, further comprising the step of calculating mc% for each site of the plurality of test sites.

4. The method of claim 1, further comprising the steps of:
   (h) at each site of the plurality of test sites, determining the following quantities:
      the count of cells (tcc) applied at the first surface of the membrane in the plurality of cells of the first fluid sample,
      the number of cells (umc) in the first fluid sample after incubation, wherein umc is proportional to $U_2$,
      the number of cells (cmc) that have migrated through the membrane pores and into the second fluid sample, wherein cmc is proportional to $L_2$,
      the percent of cells (cmc%) that have migrated through the membrane pores and into the second fluid sample, wherein cmc%=(cmc/tcc),
      the number of cells (pmc) inside the membrane pores, wherein pmc=(tcc−(umc+cmc)),
      the percent of cells (pmc%) inside the membrane pores, wherein pmc%=(pmc/tcc),
      the number of migrated cells (mc) by calculating with at least one of the formulas (mc=cmc+pmc) and (mc=tcc−umc), and
      the percent of migrated cells (mc%), wherein mc%=(me/tcc);
   (i) calculating averages of the quantities for sets of replicate test sites within the plurality of test sites; and
   calculating the coefficient of variation across the plurality of test sites.

5. The method of claim 4, wherein the first fluid sample and the second fluid sample in a portion of the plurality of test sites are cell suspensions in a serial dilution.

6. The method of claim 1, further comprising, prior to the step of incubating the cell activity assay apparatus, the steps of:
   (i) directing a first initial beam of electromagnetic radiation having a first wavelength toward the first surface of the membrane;
   (ii) measuring an initial first quantity ($U_1$) of electromagnetic radiation having a second wavelength thereby emitted;
   (iii) directing a second initial beam of electromagnetic radiation having a first wavelength toward the second surface of the membrane; and (iv) measuring an initial second quantity ($L_1$) of electromagnetic radiation having a second wavelength thereby emitted.

7. The method of claim 6, further comprising the steps of:
(h) at each site of the plurality of test sites, determining the following quantities:
the count of cells (tcc) applied at the first surface of the membrane in the plurality of cells of the first fluid sample, wherein tcc is proportional to $U_1$,
the number of cells (umc) in the first fluid sample after incubation, wherein umc is proportional to $U_2$,
the number of cells (cmc) that have migrated through the membrane pores and into the second fluid sample, wherein cmc is proportional to ($L_2-L_1$),
the percent of cells (cmc%) that have migrated through the membrane pores and into the second fluid sample, wherein cmc%=(cmc/tcc),
the number of cells (pmc) inside the membrane pores, wherein pmc=(tcc−(umc+cmc)),
the percent of cells (pmc%) inside the membrane pores, wherein pmc%=(pmc/tcc),
the number of migrated cells (mc) by calculating with at least one of the formulas (mc=cmc+pmc) and (mc=tcc−umc), and
the percent of migrated cells (mc%), wherein mc%=(mc/tcc);
(i) calculating averages of the quantities for sets of replicate test sites within the plurality of test sites; and
(j) calculating the coefficient of variation across the plurality of test sites.

8. The method of claim 1, wherein the membrane pores traverse the membrane from the first surface to the second surface at an angle $\alpha$ between about 15° and about 70° with respect to a line normal to the first surface.

9. The method of claim 8, wherein the angle $\alpha$ is between about 44° and about 46°.

10. The method of claim 8, wherein the angle $\alpha$ is such that a detection beam of electromagnetic radiation that is substantially normal to the first surface does not pass between the first surface and the second surface without being at least partially blocked by the opaque film.

11. The method of claim 8, wherein the angle $\alpha$ is such that a detection beam of electromagnetic radiation that has a range of angles of incidence substantially normal to the first surface of the membrane does not pass between the first and second surfaces.

12. The method of claim 8, wherein the angle $\alpha$ is greater than or equal to an angle $\phi$, wherein the angle $\phi=\sin^{-1}(pd/mt)$, and wherein pd is a pore diameter and mt is a membrane thickness.

13. The method of claim 7, wherein the angle $\alpha$ is greater than a sum of an angle $\beta$, and an angle $\theta$, wherein the angle $\beta$ is a maximum angle of incidence of the first beam and the second beam with respect to the line normal to the first surface, and the angle $\theta=\sin^{-1}((pd\times\cos\beta)/mt)$, wherein pd is a pore diameter and mt is a membrane thickness.

14. The method of claim 1, further comprising the step of killing the plurality of cells, wherein killing the plurality of cells is initiated after the incubating step of claim 1.

15. The method of claim 14, wherein the plurality of cells are killed by irradiating the plurality of cells with a quantity of electromagnetic radiation.

16. The method of claim 15, wherein the electromagnetic radiation has a wavelength between about 200 nanometers and about 400 nanometers.

17. The method of claim 1, further comprising the step of immobilizing the plurality of cells, wherein immobilizing the plurality of cells is initiated after the incubating step of claim 1.

18. The method of claim 17, wherein the plurality of cells are immobilized by reducing the temperature of the plurality of cells.

19. The method of claim 17, wherein the plurality of cells are immobilized by a chemical means.

20. The method of claim 19, wherein the chemical means comprises EDTA.

21. The method of claim 1, wherein the plurality of cells of the first fluid sample is labeled with a dye.

22. The method of claim 21, wherein the dye is selected to emit electromagnetic radiation having the second wavelength when exposed to electromagnetic radiation having the first wavelength.

23. The method of claim 1, wherein the first wavelength comprises a first range of wavelengths and the second wavelength comprises a second range of wavelengths.

24. A method for assaying cell activity, comprising the steps of:
(a) providing a cell activity assay apparatus having a plurality of test sites,
wherein each test site of the plurality of test sites has a membrane that has a first surface and a second surface,
wherein the membrane separates a first fluid sample, containing a plurality of cells in contact with the first surface of the membrane, from a second fluid sample in contact with the second surface of the membrane, and
wherein the membrane is made of opaque film and has membrane pores such that cells may migrate through the membrane pores but electromagnetic radiation substantially normal to the first surface and the second surface of the membrane does not pass straight through the membrane pores;
(b) directing a first initial beam of electromagnetic radiation having a first wavelength toward the first surface of the membrane through the first fluid sample, at each site of the plurality of test sites;
(c) measuring an initial first quantity ($U_1$) of electromagnetic radiation having a second wavelength thereby emitted, at each site of the plurality of test sites;
(d) directing a second initial beam of electromagnetic radiation having a first wavelength toward the second surface of the membrane through the second fluid sample, at each site of the plurality of test sites;
(e) measuring an initial second quantity ($L_1$) of electromagnetic radiation having a second wavelength thereby emitted, at each site of the plurality of test sites;
(f) storing $U_1$ and $L_1$;
(g) incubating the cell activity assay apparatus;
(h) directing a first beam of electromagnetic radiation having a first wavelength toward the first surface of the membrane through the first fluid sample, at each site of the plurality of test sites;
(i) measuring a first quantity ($U_2$) of electromagnetic radiation having a second wavelength thereby emitted, at each site of the plurality of test sites;
(j) directing a second beam of electromagnetic radiation having a first wavelength toward the second surface of the membrane through the second fluid sample, at each site of the plurality of test sites;
(k) measuring a second quantity ($L_2$) of electromagnetic radiation having a second wavelength thereby emitted, at each site of the plurality of test sites;
(l) storing $U_2$ and $L_2$; and (m) at each site of the plurality of test sites, determining the percentage of migrated cells (mc%),
wherein the percentage corresponds to the cell activity, and
wherein mc% is proportional to at least one of the formulas:
(i) $((U_1-U_2)/U_1)$, and
(ii) $(L_2/(U_2+L_2))$.

25. The method of claim 24, further comprising the step of determining, for each test site of the plurality of test sites, the following quantities:
the count of cells (tcc) applied at the first surface of the membrane in the plurality of cells of the first fluid sample, wherein tcc is proportional to $U_1$,
the number of cells (umc) in the first fluid sample after incubation, wherein umc is proportional to $U_2$,
the number of cells (cmc) that have migrated through the membrane pores and into the second fluid sample, wherein cmc is proportional to $(L_2-L_1)$,
the percent of cells (cmc%) that have migrated through the membrane pores and into the second fluid sample, wherein cmc%=(cmc/tcc),
the number of cells (pmc) inside the membrane pores, wherein pmc=(tcc−(umc+cmc)),
the percent of cells (pmc%) inside the membrane pores, wherein pmc%=(pmc/tcc),
the number of migrated cells (mc) by calculating with at least one of the formulas (mc=cmc+pmc) and (mc=tcc−umc), and
the percent of migrated cells (mc%), wherein mc%=(mc/tcc).

26. The method of claim 25, further comprising the step of calculating averages of the quantities for sets of replicate test sites within the plurality of test sites.

27. The method of claim 25, further comprising the step of calculating the coefficient of variation across the plurality of test sites.

28. A method for assaying cell activity, comprising the steps of:
(a) providing a cell activity assay apparatus having a plurality of test sites,
wherein each test site of the plurality of test sites has a membrane that has a first surface and a second surface,
wherein the membrane separates a first fluid sample, containing a plurality of cells in contact with the first surface of the membrane, from a second fluid sample in contact with the second surface of the membrane,
wherein the second fluid sample contains solutions that influence activity of the cells of the first fluid sample,
wherein the membrane is made of opaque film and has membrane pores,
wherein the membrane pores have an angle of incidence $\alpha$ with respect to an axis substantially normal to the first surface and the second surface of the membrane, and
wherein a $\alpha$ greater than $\sin^{-1}(pd/mt)$, where pd is the diameter of the membrane pores and mt is the thickness of the membrane,
such that the cells of the first fluid sample may migrate through the membrane pores but electromagnetic radiation substantially normal to the first surface and the second surface of the membrane does not pass straight through the membrane pores;
(b) incubating the cell activity assay apparatus;
(c) directing a first beam of electromagnetic radiation having a first wavelength toward the first surface of the membrane through the first fluid sample, at each site of the plurality of test sites,
wherein the first beam of electromagnetic radiation is substantially normal to the first surface and the second surface of the membrane;
(d) measuring a first quantity ($U_2$) of electromagnetic radiation having a second wavelength thereby emitted, at each site of the plurality of test sites;
(e) directing a second beam of electromagnetic radiation having a first wavelength toward the second surface of the membrane through the second fluid sample, at each site of the plurality of test sites,
wherein the second beam of electromagnetic radiation is substantially normal to the first surface and the second surface of the membrane;
(f) measuring a second quantity ($L_2$) of electromagnetic radiation having a second wavelength thereby emitted, at each site of the plurality of test sites; and
(g) at each site of the plurality of test sites, determining the percentage of cells that have migrated through the membrane pores,
wherein the percentage is proportional to $((L_2)/(U_2+L_2))$, and
wherein the percentage corresponds to the cell activity.

29. The method of claim 28, wherein the substantially normal electromagnetic radiation, the first beam of electromagnetic radiation, and the second beam of electromagnetic radiation have an angle of incidence $\beta$ with respect to the axis normal to the first surface and the second surface of the membrane, and
wherein $\alpha$ is greater than $(\beta+(\sin^{-1}((pd\times\cos\beta)/mt))$.

30. The method of claim 29, wherein mt is between about 1 and 1000 microns,
wherein $\alpha$ is between about 15° and 70°,
wherein $\beta$ is less than about 15°,
wherein the membrane pores are of a density between about $1\times10^3$ and $1\times10^9$ pores/cm$^2$, and
wherein pd is less than or equal to mt and is between about 1.0 and 14.0 microns.

31. The method of claim 28, wherein mt is between about 1 and 1000 microns,
wherein $\alpha$ is between about 15° and 70°,
wherein the membrane pores are of a density between about $1\times10^3$ and $1\times10^9$ pores/cm$^2$, and
wherein pd is less than or equal to mt and is between about 1.0 and 14.0 microns.

32. The method of claim 31, wherein the opaque film blocks more than about 99.0% of electromagnetic radiation in a wavelength range between about 400 and 580 nanometers,
wherein mt is about 31 microns,
wherein pd is about 8 microns,
wherein $\alpha$ is between about 44° and 46°,
wherein the first wavelength of the first beam and the first wavelength of the second beam are about 485 nanometers, and
wherein the second wavelength of the first quantity and the second wavelength of the second quantity are about 530 nanometers.

33. The method of claim 28, wherein the opaque film blocks more than about 99.0% of electromagnetic radiation in a wavelength range between about 400 and 580 nanometers.

34. The method of claim 28, wherein the first fluid sample is one of a positive control, a negative control, a sample, and a cell suspension of the sample in serial dilution, and wherein the second fluid sample is one of a cell suspension and a cell suspension in serial dilution.

35. The method of claim 34, wherein the method further comprises the step of compensating for measurement error by determining, at each site of a plurality of sites having a cell suspension in serial dilution, the proportion of at least one of $U_2$ and $L_2$ with respect to a number of cells applied at the each site, and comparing the proportions of the plurality of sites having a cell suspension in serial dilution.

36. The method of claim 34, further comprising the step of comparing sites having the positive control first fluid sample, sites having the negative control first fluid sample, and sites having the first fluid sample.

* * * * *